(12) United States Patent
Scheven (10) Patent No.: US 7,180,288 B2
(45) Date of Patent: Feb. 20, 2007

(54) DOWNHOLE NMR FLOW AND FORMATION CHARACTERIZATION WHILE SAMPLING FLUIDS

(75) Inventor: Ulrich Scheven, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/985,476

(22) Filed: Nov. 10, 2004

(65) Prior Publication Data

US 2006/0097722 A1    May 11, 2006

(51) Int. Cl.
*G01V 3/00*    (2006.01)
(52) U.S. Cl. ............................ 324/303; 324/300
(58) Field of Classification Search ............... 324/303, 324/300, 307, 308
See application file for complete search history.

(56) References Cited

U.S. PATENT DOCUMENTS

| | | | |
|---|---|---|---|
| 4,689,560 A | 8/1987 | Nayler et al. | 324/306 |
| 5,298,861 A | 3/1994 | Sugimoto | 324/306 |
| 6,392,409 B1 | 5/2002 | Chen | 324/303 |
| 6,518,758 B1 | 2/2003 | Speier et al. | 324/303 |
| 6,528,995 B1 * | 3/2003 | Speier et al. | 324/303 |
| 6,531,869 B1 * | 3/2003 | Speier et al. | 324/303 |
| 6,538,438 B1 | 3/2003 | Speier et al. | 324/303 |
| 6,570,382 B1 | 5/2003 | Hurlimann et al. | 324/303 |
| 6,642,715 B2 * | 11/2003 | Speier et al. | 324/303 |
| 6,710,596 B2 | 3/2004 | Speier et al. | 324/303 |
| 6,856,132 B2 * | 2/2005 | Appel et al. | 324/303 |
| 6,897,652 B2 * | 5/2005 | Appel et al. | 324/303 |
| 6,956,371 B2 * | 10/2005 | Prammer | 324/303 |

FOREIGN PATENT DOCUMENTS

GB    2 407 167 A    4/2005

OTHER PUBLICATIONS

Carr, H. Y. et al. "Effects of Diffusion on Free Precession in Nuclear Magnetic Resonance Experiments". *Phys. Rev.*, vol. 94, No. 3, pp. 630-638 (May 1954).
Casanova, F. et al. "Velocity distributions measured with a single-sided NMR sensor". *Journal of Magnetic Resonance*, vol. 171, pp. 124-130 (2004).
Kärger, Jörg et al. "The Propagator Representation of Molecular Transport in Microporous Crystallites". *Journal of Magnetic Resonance*, vol. 51, pp. 1-7 (1983).
Meiboom, S. et al. "Modified Spin Echo Method for Measuring Nuclear Relaxation Times". *Rev. Sci. Instrum.*, vol. 29, No. 8, pp. 688-691 (Aug. 1958).
Sodickson, A. et al. "A generalized k-space formalism for treating the spatial aspects of a variety of NMR experiments". *Prog. NMR Spectrosc.*, vol. 33, pp. 77-108 (1998).

* cited by examiner

*Primary Examiner*—Brij B. Shrivastav
(74) *Attorney, Agent, or Firm*—Vincent P. Loccisano; Jody Lynn DeStefanis; Dale Gaudier (57) ABSTRACT

A method of measuring characteristics of a flowing fluid is described including: (a) providing a flowing fluid; (b) applying a static field gradient to the flowing fluid; (c) applying a series of nuclear magnetic resonance pulses to the flowing fluid; (d) detecting signals from the flowing fluid, wherein the signals are generated in response to the nuclear magnetic resonance pulses; and (e) analyzing the real and imaginary components of the signals to determine one or more characteristics of the flowing fluid. Also described is an apparatus for implementing this method.

44 Claims, 9 Drawing Sheets

No flow

Figure 7(c)

Flow

DOWNHOLE NMR FLOW AND FORMATION CHARACTERIZATION WHILE SAMPLING FLUIDS

FIELD OF THE INVENTION

The present invention relates to a nuclear magnetic resonance (NMR) method and apparatus, and more particularly, to an NMR method and apparatus for measuring fluid flow and determining characteristics of the flow field, the flowing fluid, and the media surrounding the fluid.

BACKGROUND OF THE INVENTION

Nuclear magnetic resonance (NMR) methods are well established in the laboratory to measure fluid flow in pipes, rocks, and biological systems. Typically, flow is measured by encoding molecular displacements in the phase of nuclear spins in the (flowing) fluid, during an evolution interval $\Delta$. An encoding and decoding of the spin's position before and after interval $\Delta$ is affected by means of static or pulsed field gradients. The NMR signal is measured for either a range of phase encoding times or a range of gradient strengths, or both, and then analyzed. For small static or pulsed field gradient strengths or encoding times, the shift of the phase of the NMR signal is proportional to the velocity and the time which has elapsed between the encoding and the decoding steps. The complete probability distribution of molecular displacements during the evolution period $\Delta$ can be obtained from pulsed field gradient-NMR (PFG-NMR) by extending the measurements to larger pulsed field gradient strengths, then Fourier transforming the data. The PFG-NMR type of experiment has been called NMR-scattering in the published literature, and the extraction of probability distributions from such experiments is commonly referred to as a measurement of the propagator in the published literature.

NMR measurements are also commonly used in the borehole to probe the NMR decay behavior of the stationary fluid in the reservoir rock. In these techniques, magnetic fields are established in the formation using suitably arranged permanent magnets. These magnetic fields induce nuclear magnetization, which is flipped and otherwise manipulated using on-resonance radio frequency (RF) pulses. NMR echoes are observed, and their dependence (of their magnitude) on pulse parameters and on time is used to extract information about the formation and the fluids in it.

Fluids are routinely sampled in the borehole using various fluid samplers, such as Schlumberger's MDT™ module. The MDT™ tool includes at least one fluid sample bottle, a pump to extract the fluid from the formation, and a contact pad having a hole. When the device is positioned proximate a region of interest, the pad is pressed against the borehole wall, making a tight seal. Fluid in the formation is induced to flow, by pumping fluid out of the formation through the hole in the pad. When the operator is convinced that the fluid is 'pure' reservoir fluid (i.e., the sample includes acceptable levels of mud or other contaminants), a sample of the fluid is either analyzed in-situ or placed into a sample bottle for later analysis. The module is then moved to the next region of interest. Information regarding the movement of fluid in the formation during the pumping process ("pumpout") can provide valuable information related to formation and fluid sample properties.

Fluid flow towards the borehole is also routinely produced during pressure testing, essentially in the same manner as described for the MDT™ tool described above. Accordingly, useful information may be similarly obtained during this process.

To date, there is no method or apparatus to obtain information regarding the fluid flow or the formation during these induced fluid flow scenarios. Accordingly, it is an object of the present invention to provide an NMR method to probe the flow which occurs inside the formation during fluid pumpout.

SUMMARY OF THE INVENTION

The present invention combines conventional techniques for analyzing flow rate of a flowing fluid and in particular a fluid within a porous media (such as tissue, rock, soil, food, wood, etc.). The presented method and apparatus is suited for use in chemical applications such as where fluid in a pipe or in molecular seives is analyzed, biological system such as where bodily fluids are analyzed, and in food processing systems such as where water or other liquids are analyzed in the food. In addition, this method and apparatus is suited for system involving the withdrawal of fluids from the formation with an NMR measurement on the fluid flow occurring inside the formation induced during fluid pumpout, fluid invasion (including gas lift, mud infiltration), etc. The measurement can be used to determine the probability distribution for flow displacements, also known as propagators, and can provide a quantitative measure of permeability anisotropy, and the presence or absence of flow channels, cracks, and trapped fluids. The measurement can be used to detect the flow of drilling fluid or formation fluid. It also permits scattering type NMR measurements, which can probe the size of the grains proximate the flowing fluid. In one embodiment of the present invention, a method of measuring characteristics of a flowing fluid is disclosed, comprising: (a) inducing a fluid to flow; (b) applying a static field gradient to the flowing fluid; (c) applying a series of nuclear magnetic resonance pulses, which are also referred to as pulses of oscillating electromagnetic fields, to the flowing fluid; (d) detecting signals from the flowing fluid, wherein the signals are generated in response to the nuclear magnetic resonance pulses; and (e) analyzing the in-phase and quadrature components of the signals to determine one or more characteristics of the flowing fluid. In addition, pulsed field gradients may also be used, for instance, in combination with, the static field gradients. The fluid may be actively induced to flow such as by activating a pump or passively induced to flow such as by allowing fluids (such as drilling muds) to invade the area. This method may be used to determine the flow rate of the fluid in a pipe or a porous media. In a preferred method, the fluid is pumped into a flowline within a tool wherein the tool is equipped with means to impart the static field gradient as well as the oscillating magnetic field pulses.

In one oilfield services application of the present method, the data may be used to collect information regarding the integrity of the contact between the tool and the borehole wall. Likewise, the method may be useful in assessing the integrity of the borehole wall. The method may be further used to identify any localized velocity fields in the earth formation (or other porous media), the isotropy of permeability of the earth formation (or other porous media), or the lithology of the earth formation (or other porous medium).

The nuclear magnetic resonance pulse-sequences may include modified Carr-Purcell (CP) sequences or modified Carr-Purcell-Meiboom-Gill (CPMG)-like sequences and may be combined with either stimulated echoes or Hahn echoes. For the purposes of the present patent application, modified CPMG and modified CP sequences are defined as CPMG or CP pulse sequences wherein the initial excitation is provided by stimulated echoes or spin echoes rather than the traditional 90 degree pulse. Accordingly, the modified CPMG and modified CP sequences used herein are distinguished by the phase of the refocusing pulses relative to the phase of the magnetization produced by the spin echo or stimulated echo. As described in more detail below, the stimulated echoes or the Hahn echoes of the modified CP or modified CPMG sequences can employ variable encoding times.

The method may include the detection of the in-phase (real) and the quadrature (imaginary) components of the detected stimulated echoes or Hahn-echoes. Signals refocused by modified Carr-Purcell and modified Carr-Purcell-Meiboom-Gill sequences may be combined to produce a complex echo train and the real and imaginary parts of the complex echo train analyzed to determine the flow rate and characteristics of the flow field of the fluid in the earth formation. The relationship between spatial magnetization wave vector (k), the flow field, and the real and imaginary parts of the complex echo train amplitudes may be developed for two or more different values of k or by using one value of k and measuring flow field at zero velocity and at one or more finite velocities.

In a second embodiment a nuclear magnetic resonance apparatus to measure characteristics of a flowing fluid, comprising: an antenna to create an oscillating magnetic field on a flowing fluid, wherein the antenna is connected to a controller; a magnet creating a static field gradient to the flowing fluid; means to detect signals from said flowing fluid generated in response to the oscillating magnetic field; and processing means to analyze the in-phase (real) and quadrature (imaginary) components of the signals to determine one or more characteristics of the flowing fluid. The apparatus may further comprise means to induce the fluid to flow. It is noted that in oilfield drilling environments, the presence of drilling fluids will induce the formation fluid to flow. Likewise, in medical applications no separate inducing means may be required; for example, if blood is the fluid of interest, no separate "pumping" will be required to induce the flow.

The processing means may be programmed to determine the flow rate of the fluid in the fluid-filled earth formation and/or in the flowline during pumping using the signals. The processing means may further include means for determining the probability distribution for molecular displacements of the fluid in the fluid-filled earth formation during pumping. Likewise, the processing means may be further programmed to compare the flow rate of the fluid in flowline and the flow rate of the fluid in the earth formation to determine the integrity of the contact between the tool and the borehole wall or to determine the integrity of the borehole wall itself. The processing means may be further programmed to compare these flow rates to determine the lithology of the earth formation. The processing means is further programmed to analyze the flow rate of the fluid in the earth formation to identify any localized velocity fields in the earth formation and the isotropy of permeability of the earth formation.

In accordance with the present invention, a permanent magnet is mounted inside or behind the contact pad, along with an NMR coil which can be placed around the inlet hole of the pad, or an array of antennas (each measuring the NMR signal at different points in the formation) or a surface coil.

The magnet is shaped to suit the measurement needs. For example, it would preferably be designed to produce a uniform gradient inside the formation and in front of the fluid inlet of the contact pad. The NMR coil is tuned to be on-resonance at one or several shells (i.e., locations in the formation), providing the capability for coarse flow imaging Spin-echo, also called Hahn echo (HE), and stimulated echo (STE) measurements, optionally followed by modified Carr-Purcell-Meiboom-Gill (CPMG) and modified Carr-Purcell (CP) echo trains may be used (and controlled using the controller means). The fluid may be withdrawn at variable velocities depending on the type of information desired. The flow in shells at different depths of investigation may also be measured.

Further features and applications of the present invention will become more readily apparent from the figures and detailed description that follows.

BRIEF DESCRIPTION OF THE DRAWINGS

FIGS. 6(a)–(d) are graphs showing representative stray field echo trains on water in a Bentheimer core sample, wherein FIGS. 6(a) and 6(b) are in the absence of flow and FIGS. 6(c) and 6(d) are in the presence of flow.

DETAILED DESCRIPTION

The present invention applies NMR principles to fluid during pumpout to extract formation characteristics together with characteristics of the flow field and is particularly useful for the following oilfield applications:

1. Sample control: If the measured flow at some distance inside the formation is lower than expected for the pumping speed, then this measurement will indicate that drilling fluid is invading the fluid sampler, possibly because the seal of the pad against the formation wall is inadequate, or because the formation wall may be damaged or cracked allowing for flow to bypass the seal.

2. Formation characterization: If the measured flow at some distance inside the formation is higher than expected, then the formation may have highly anisotropic permeability, such as due to the presence of an impermeable layer just above or below the point where the fluid is withdrawn. High flow rates at different depths may also indicate flow in channels or cracks, i.e. a localized velocity field. The dependence of flow velocities on depths of investigation can be used to invert for vertical and horizontal permeability, using model-based inversion techniques.

3. Lithology (1): Highly variable flow regimes between different shells may also indicate damage or anisotropic permeability or lithology with coarse structure on the scale of the inter-shell spacing of the measurement.

4. Lithology (2): Wide and skewed fluid displacement distributions within a shell indicate a heterogeneous pore space, with implications for identifying lithology and estimating recovery factors.

5. Trapped fluid: The amount of fluid trapped in the formation by capillary forces or heterogeneity of the pore space can be quantified from the measurement of the probability distribution of molecular displacements.

The method and apparatus of the present invention may be likewise used during drilling. In such an application fluid flows radially outward from the borehole into the formation inducing the formation fluid to flow. Similar, the method and apparatus may be used in leakoff situations where the pressure in the borehole is larger than that in the formation and there is poor or no filter cake separating the two. For example, during quiet time of the tool, the flow of the invading drilling mud may be measured.

A range of magnet/flowline designs can be used to implement the present invention. Appropriate magnet design criteria are similar to those used in the design of logging tools and flow measurement tools with constant gradients, such as Schlumberger's MRX™ tool. Ideal designs will establish a magnetic field in that section of the formation where flow is expected. In particular the static magnetic field and the oscillating magnetic field produced by the NMR coil are predominantly perpendicular to each other in the region of interest, and the gradient of the static magnetic field is predominantly co-linear with the flow direction, i.e. pointing radially inward towards the sampling hole.

Figure 1:
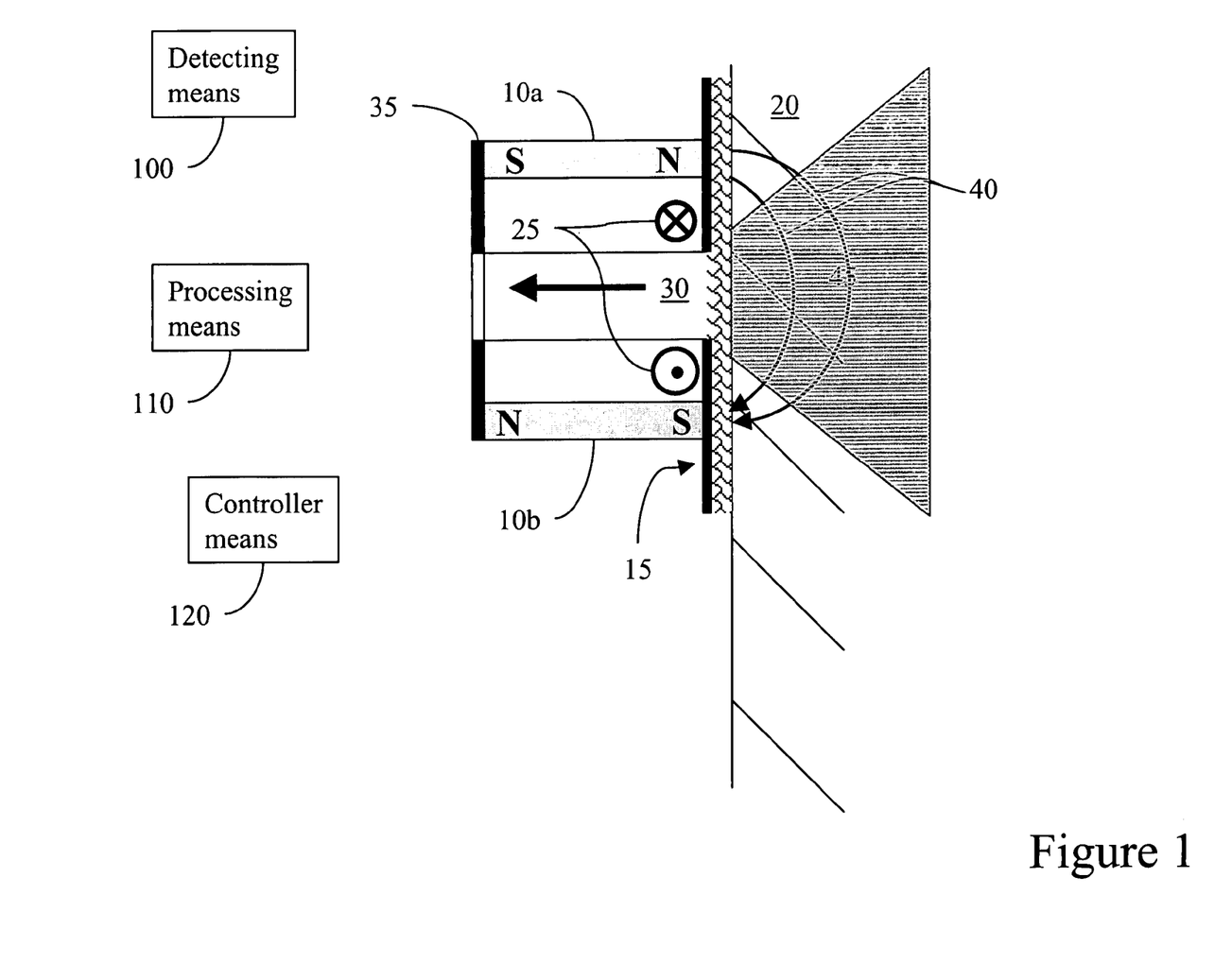
FIG. 1 is a schematic cross-sectional side view of one embodiment of the present invention.

As shown in FIG. 1, two bar magnets 10a, 10b establish a magnetic field in the formation 20 in the area in front of the sampling hole of the contact pad 15 as shown by the shaded region 45. An antenna 25 (in this embodiment, a coil) is placed at the mouth of the flow line 30. A flux return plate 35 behind the magnets 10a, 10b is designed to shape the field such that fluid behind the antenna 25 (or elsewhere outside the formation) does not contribute to the NMR signal (detected using detecting means 100 known in the art). The magnetic field in the formation is indicated by the field lines 40.

The oscillating magnetic field produced by the antenna 25 is pointing in the radial direction, perpendicular to the contact plate and the static field in front of the sampling hole of the contact pad 15. The antenna 25 can operate at different frequencies, allowing radial imaging of the fluid velocity. Different antenna designs and locations are possible. Additional antennas (not shown in the figure) can easily be installed to probe flow elsewhere. For example, one or more NMR antennas may be installed in or near the contact pad 15 to probe the motion of the fluid spins in the anticipated flow field. The flow velocity is spatially resolved in the radial direction by operating in different shells (or regions in the formation). Placing several NMR antennas along the contact pad 15 provides spatial resolution in the vertical direction, i.e. along the borehole, and away from the sampling hole in the pad 15.

Also shown in FIG. 1 are detecting means 100 for detecting NMR signals, processing means 110 for processing the signals and a controller means 120 for controlling the generation of NMR sequences. Each of these elements are known in the art and will not be described in further detail.

The method (as described in more detail below) and apparatus of the present invention was tested on a Bentheimer rock sample using the experimental set-up shown in FIG. 2. Testing was conducted in the fringe field of a super-conducting magnet 10. These measurements establish that the present invention may be used in grossly inhomogeneous fields characteristic of the fringe field of the super conducting-magnet, and therefore also in those characteristic of a logging tool, such as Schlumberger's MRX™ tool, and of other tools having an "inside out" NMR flow.

A cylindrical Bentheimer rock core (having a diameter of approximately 48 mm) was sealed on its curved outer surface using epoxy, while distributor caps with inlets were glued to ends of the core. Water was flowed into the core through the distributor caps using a piston pump. In this manner axial flow with controllable mean velocity was established. Flow measurements were performed with flow velocities of 0.41 mm/sec and flow evolution times of 320 ms.

Figure 2:
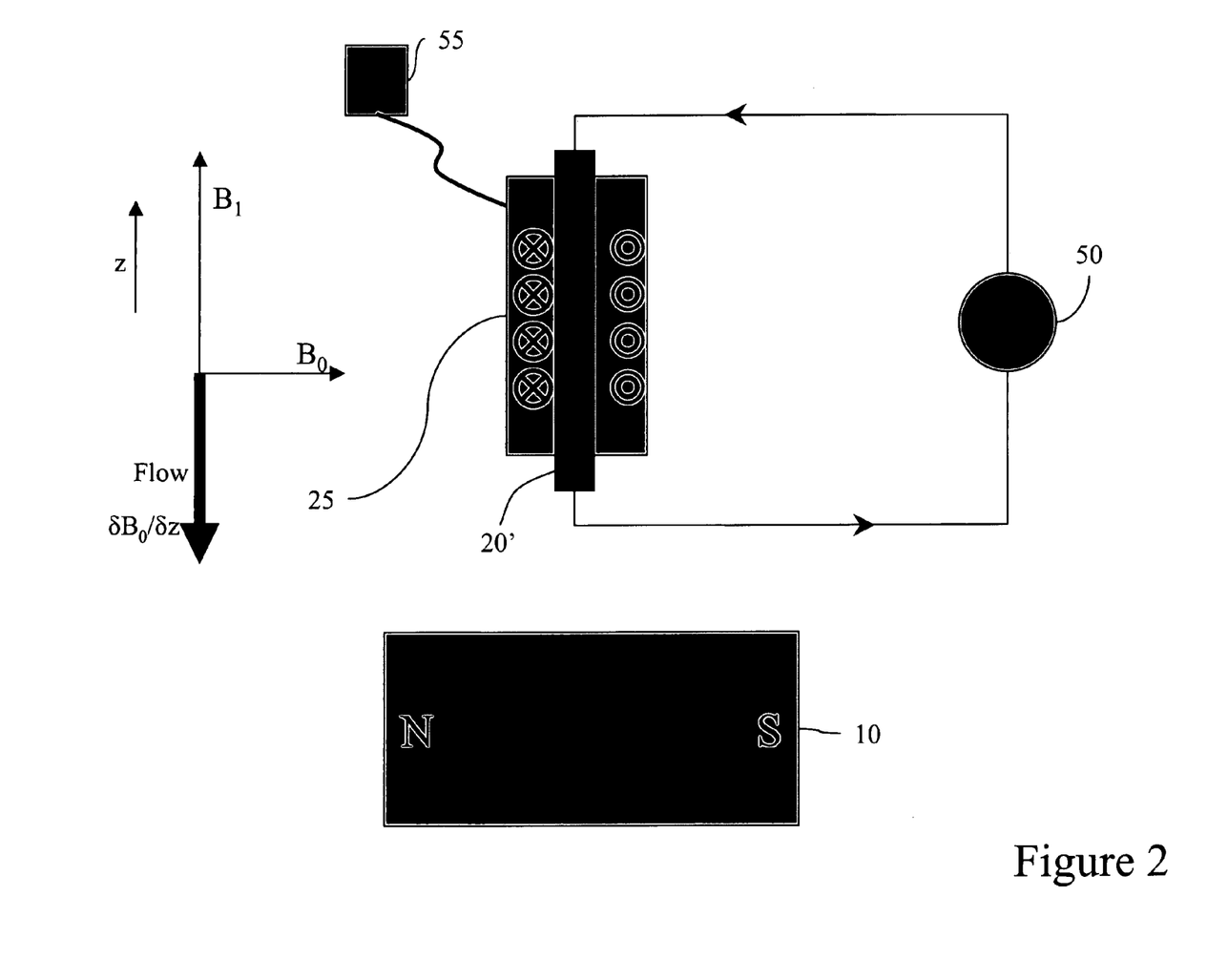
FIG. 2 is a schematic top view of the experimental setup used in the laboratory to demonstrate the workings of the invention, showing the relative orientation of static ($B_0$) and RF ($B_1$) fields, the gradient $\partial B_0/\partial_z$ of the static field, and the flow direction, all of which are oriented as in the present invention.

As shown in FIG. 2, the rock core 20' was placed inside the solenoid of a 1.765 MHz tuned circuit which served as the NMR antenna 25. The axis of the rock, fluid flow, and solenoid were co-linear, aligned with the gradient of the magnetic field as shown in FIG. 2. The gradient along the flow direction was measured to be 13.8 gauss/cm. At the center of the rock core 20' the field strength $B_0$ was approximately 414 gauss corresponding to the NMR antenna's resonance frequency of 1.765 MHz. FIG. 2 also shows the relative orientation of static ($B_0$) and RF ($B_1$) magnetic fields, the field gradient ($\partial B_0/\partial z$), and the flow direction. Fluid displacements along the direction $\partial B_0/\partial z$ were detectable. The relative orientation of these quantities is the same as that shown in FIG. 1.

The superconducting magnet 10 was positioned perpendicular to the flow, producing a magnetic field $B_0$ perpendicular to the flow at the sample 20', with a field gradient parallel to the flow. A pump 50 was used to produce steady flow conditions similar to those produced by an MDT™ tool, and a spectrometer 55 was used to conduct the NMR measurements by controlling the timing, phase and power of the RF pulses and collecting the data.

The detection of molecular displacements by NMR, using a combination of RF pulses and static or pulsed field gradients, is standard practice and well understood in the laboratory, where static fields are homogeneous. It has also been applied to grossly inhomogeneous fields, where diffusion editing with either stimulated echoes (STE) or Hahn echoes (HE), followed by a modified CPMG pulse train, as described in commonly owned U.S. Pat. No. 6,570,382 (incorporated by reference herein in its entirety). It is noted that pulsed field gradients may be employed in conjunction with the static field gradients disclosed herein to alter the strength or direction of the flow encoding gradients. In this configuration additional gradient coils such as that described in Casanova et al., "Velocity distributions measured with a single sided NMR sensor," Journal of Magnetic Resonance Vol. 171, pages 124–130 (2004) (incorporated by reference herein in its entirety) may be used as well as gradient amplifiers. Pulsed field gradients could also be used to spoil the signal from regions where one wishes to suppress the signature of flow or from unwanted coherences.

Figure 3A:
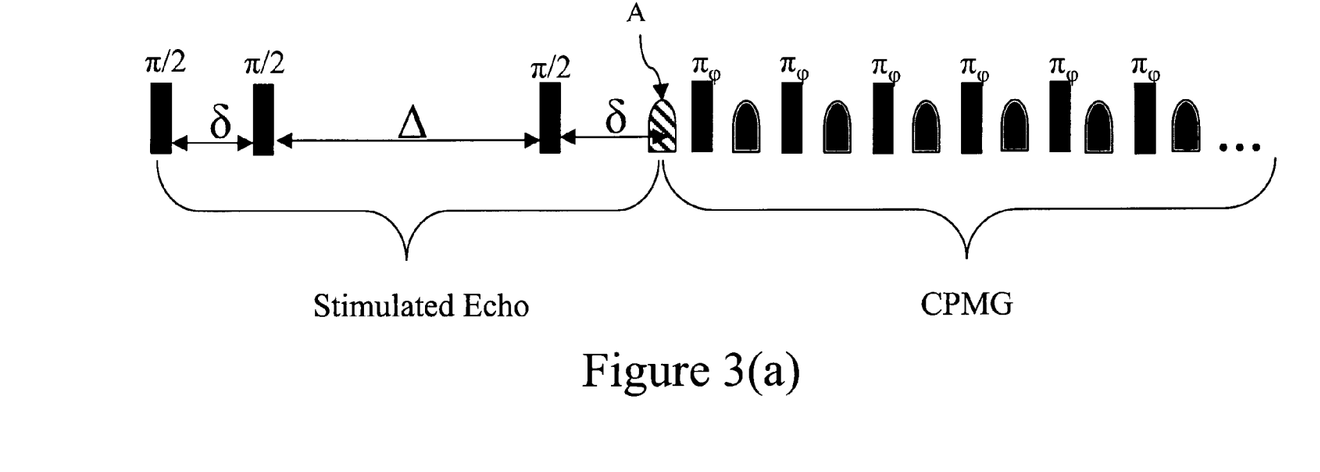
FIGS. 3(a) and (b) are schematics showing the STE-CPMG sequence and STE-CP sequence, respectively: (a) in-phase detection, $\pi$-pulses with phase $\phi$ (CPMG) and (b) quadrature detection, $\pi$-pulses with phase $\phi'=\phi+\pi/2$ (CP).
Figure 3B:
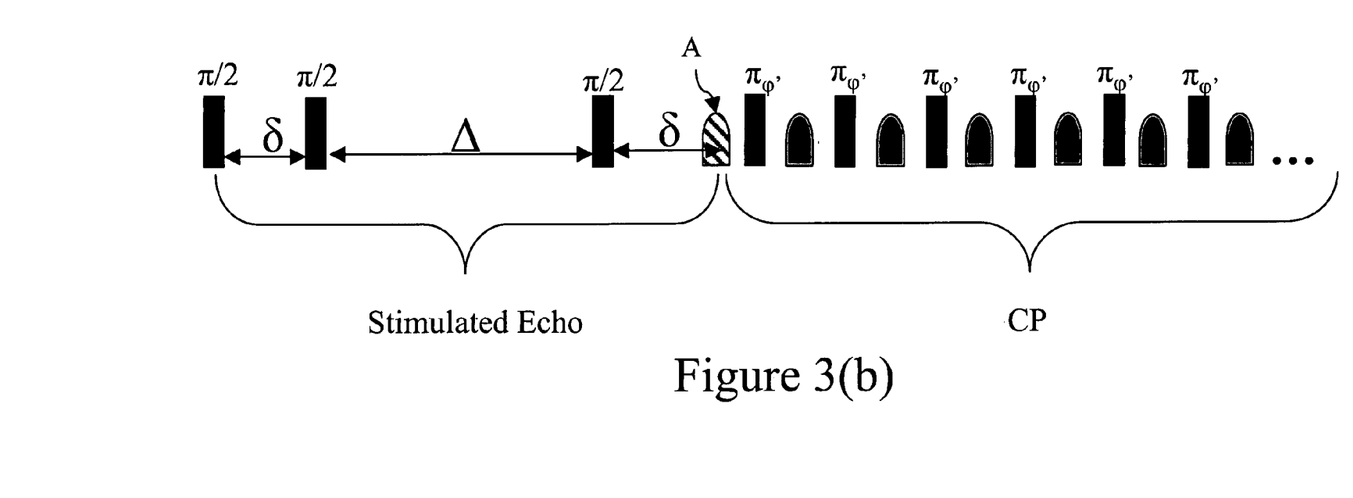

The detection and characterization of the flow field described here uses two sequences, STE-CPMG and STE-CP (as shown in FIGS. 3(a) and (b), respectively) employed to detect the in-phase and quadrature components of the stimulated echo. Both sequences use refocusing pulses, which make possible the repeated measurement of signal between these refocusing pulses, as known in the art. (See Carr et al., "Effects of diffusion on the free precession in nuclear magnetic resonance experiments," Phys. Rev. Vol. 94, pages 630–638 (1954). and Meiboom et al., "Modified spin echo method for measuring nuclear relaxation rates," Rev. Sci. Instrum. Vol. 19, pages 688–691 (1958), incorporated by reference herein in their entireties.) The CP refocusing pulses have a rotated phase (with respect to the in-phase detection of the refocusing π pulses of the CPMG echo train). The phase is rotated by $\phi_r = \pi/2$ with respect to the π-pulses of the in-phase detection. The echo trains produced by the modified CPMG and modified CP acquisitions are combined to produce the complex (real and imaginary) echo train. The essential difference between diffusion-editing acquisitions (see U.S. Pat. No. 6,570,382) and the flow acquisitions is the detection of the quadrature signal in addition to the in-phase signal. The physical reason for the presence of a quadrature signal is that flow breaks the symmetry of molecular displacements.

Although less efficient, quadrature detection could also be affected using rotation angles $\phi_r$ not equal to $\pi/2$. Hence, any non-zero value of $\phi_r$ may be used. While quadrature detection with CP trains have been used for stray field imaging, they have not been applied to measurement of flow without pulsed field gradients in grossly inhomogeneous fields. [They have been used for the measurement of flow in grossly inhomogeneous magnetic fields, but only in conjunction with pulsed field gradients, see Casanova et al.].

In the presence of static field gradient g, the stimulated echo (STE) with spatial encoding interval δ and storage interval Δ will be proportional to:

$$STE = \langle e^{ik\zeta_i} \rangle \quad (1a)$$

$$k = \gamma \delta g \quad (1b)$$

where k is the spatial magnetization wave vector; γ is the gyro-magnetic ratio of protons; g is the strength of the field gradient; and $\zeta_i$ is the displacement of a proton i during the evolution of time Δ+Order(δ). The stimulated echo is proportional to the ensemble average of the phase factor over all magnetized protons.

FIGS. 3(a) and (b) show the pulse sequences used for the acquisition of the in-phase and the quadrature signal of the stimulated echo A. The three π/2 pulses produce a stimulated echo, whose real and imaginary parts are refocused by the CPMG and CP refocusing trains of pulses. In the presence of flow along the static field gradient the magnitudes of the in-phase and out-of-phase components of the stimulated echo will depend on δ and Δ as conventionally understood in the art, see Equations (1a) and (1b).

Figure 4A:
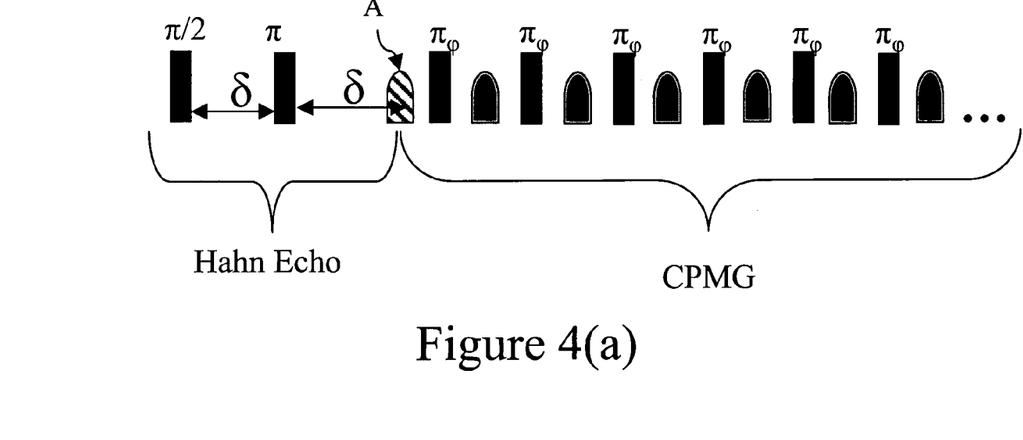
FIGS. 4(a) and (b) are schematics showing the HE-CPMG sequence and HE-CP sequence, respectively: (a) in-phase detection, $\pi$-pulses with phase $\phi$ (CPMG) and (b) quadrature detection, $\pi$-pulses with phase $\phi'=\phi+\pi/2$ (CP).
Figure 4B:
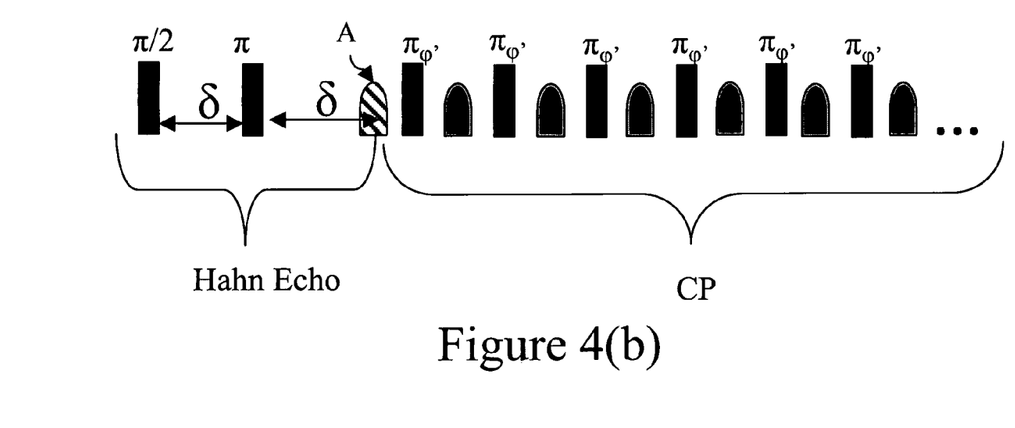

FIGS. 4(a) and (b) are schematics of alternative pulse sequences for acquisition of the in-phase and the quadrature signal of the stimulated echo A which may be applied to the present method. In the presence of flow along the static field gradient, the magnitudes of the in-phase and out-of-phase components of the Hahn-echo will depend on δ.

Figure 5A:
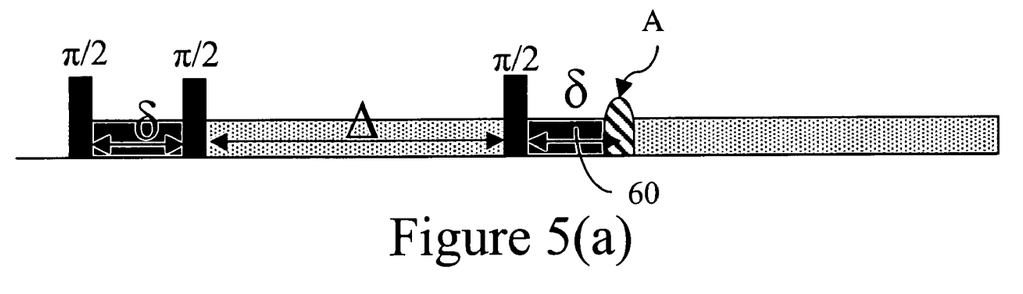
FIGS. 5(a)–(c) are schematics showing: (a) stray field STE, (b) ordinary PFG-STE, and (c) bipolar PFG-STE.
Figure 5B:
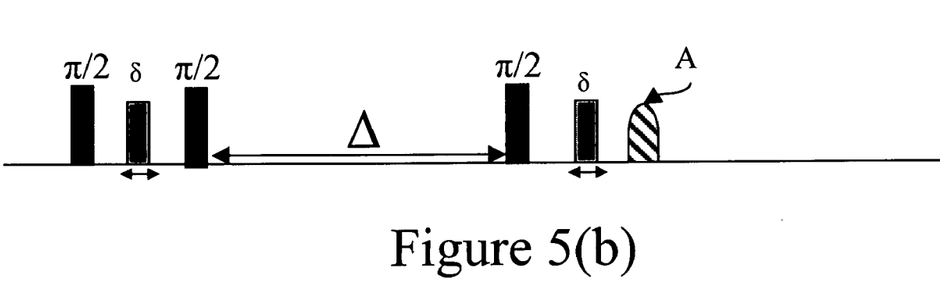

The stray field sequence shown in FIG. 5(a), with the encoding/decoding static field gradient indicated by the solid grey bar B, closely resembles the ordinary PFG-STE sequence shown in FIG. 5(b), with the encoding/decoding pulsed field gradient indicated by the hatched area C. Sequence 5(b) is commonly used when disturbing background fields are negligible in the sample. The bipolar sequence shown in FIG. 5(c) compensates for internal gradients in the rock and is commonly used in the lab when measuring NMR on fluids in rocks. The magnetization k-vector by which molecular displacements are encoded is proportional to the solid greyed area B that is the product of effective gradient duration and gradient strength. In stray field experiments, k is varied by varying δ. In PFG sequences, k is varied by changing either δ or the gradient strength or both.

Pulse field gradients can be employed in conjunction with the present method, if gradient coils are used and connected to the requisite gradient amplifiers. The pulsed field gradients can then be applied during the coding intervals (see little delta, δ in FIGS. 3 and 4) to alter the strength and modify the direction of the effective displacement encoding gradient, which, in the absence of gradient pulses, is set by the static gradient alone. It is also possible to apply pulse sequences such as a bi-polar pulsed field gradient sequence of FIG. 5(c), followed by modified CPMG or modified CP echo trains. The effect of the static gradient is cancelled altogether, and it is not used to encode displacement information; in this case, only the pulsed field gradients encode for displacements. Such a technique has been employed by Casanova et al. in an inside out NMR geometry, outside the borehole. However, the present inventors have discovered that this method may also be used in the borehole.

Three representative stray field echo trains acquired on water in Bentheimer are shown in FIGS. 6(a)–(d), in the presence or absence of flow acquired using STE-CPMG and STE-CP pulse sequences to measure the real and imaginary parts of the signal. The filtered binned real and imaginary parts of the echo amplitudes are plotted versus time for three representative choices of k, where k is set by the encoding interval δ and the fixed background gradient. In the absence of flow, all of the signal resides in the real channel, shown in FIG. 6(a). No signal appears in the imaginary channel, shown in FIG. 6(b). For k=89 mm$^{-1}$ the signal is suppressed by diffusion. In the presence of flow the signal transfers by the flow from the real channel (FIG. 6(c)) into the imaginary channel (FIG. 6(d)).

Figure 7A:
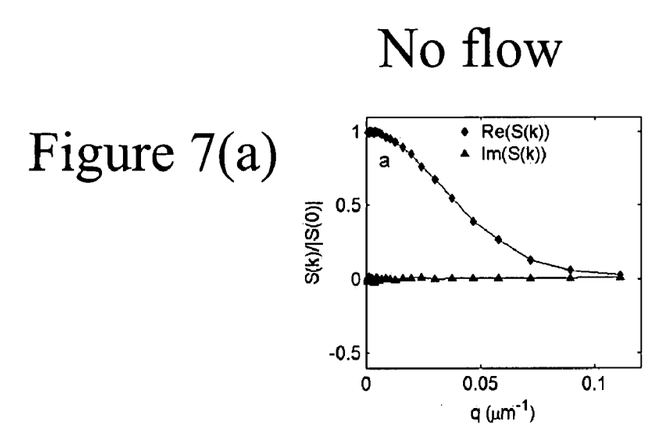
FIGS. 7(a) and 7(c) show the real and imaginary parts of the stimulated echo STE acquired with the STE-CPMG and STE-CP sequences, in the absence and presence of flow, respectively.
Figure 7B:
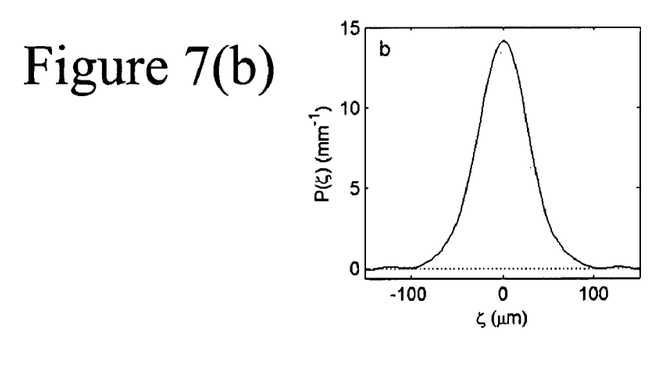
FIGS. 7(b) and 7(d) are the displacement probabilities obtained from this data by complex conjugate completion and Fourier transform.
Figure 7C:
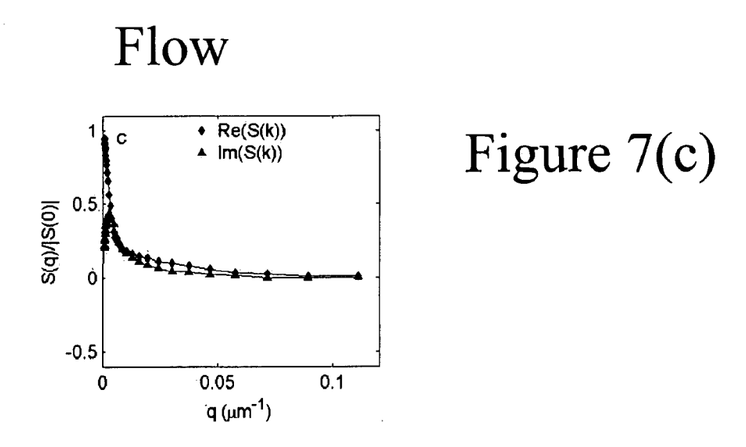
Figure 7D:
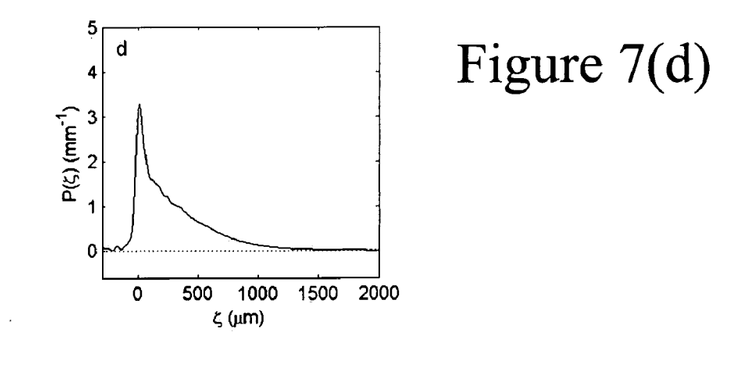

As shown in FIGS. 6(a)–(d) flow shifts the signal into the imaginary channel, and the real and imaginary parts of the stimulated echo are detected by the measurement. In order to extract a single complex echo amplitude for each choice of δ one could either fit a multi-exponential decay to the data of the FIGS. 6(a)–(d) and use the fitted amplitude at t=0, or one may just sum the echoes. The latter approach is exact for mono-exponential magnetization decay, and approximately correct when the distribution of relaxation times is reasonably narrow. This condition is met here, and the echoes are summed. In the absence of flow, increasing values of δ depress the real echo amplitude, due to molecular diffusion. In the presence of flow, some of the signal shifts into the imaginary channel and is measured in the imaginary channel. This scenario is shown in FIGS. 7(a) through 7(d). FIG. 7(a) shows the real and imaginary part of the stimulated echoes acquired with the CPMG and CP echo trains, in the absence of flow. FIG. 7(c) shows the corresponding data in the presence of flow. FIG. 7(b) shows the probability distribution for molecular displacements obtained by Fourier transform from FIG. 7(a). FIG. 7(d) shows the probability distribution, plotted against displacement ζ, for molecular displacements obtained by Fourier transform from FIG. 7(c).

Figure 5C:
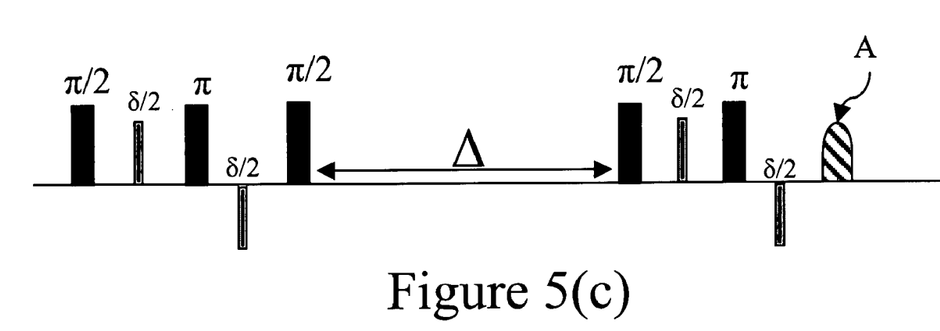
Figure 6A:
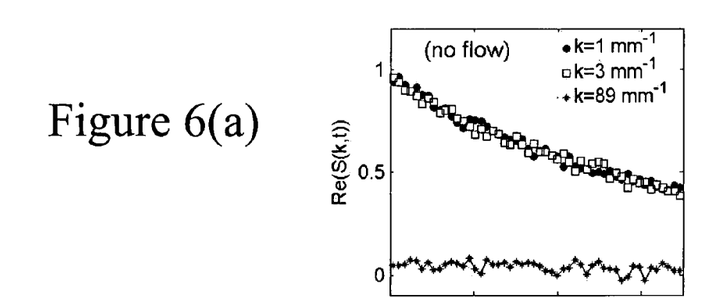
Figure 6B:
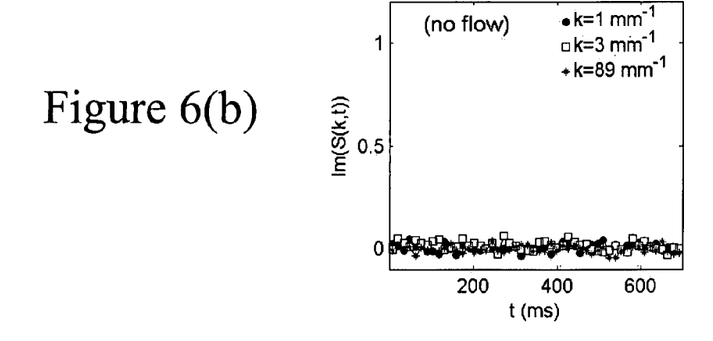
Figure 6C:
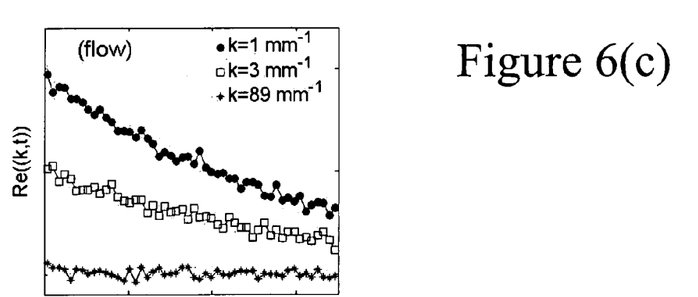
Figure 6D:
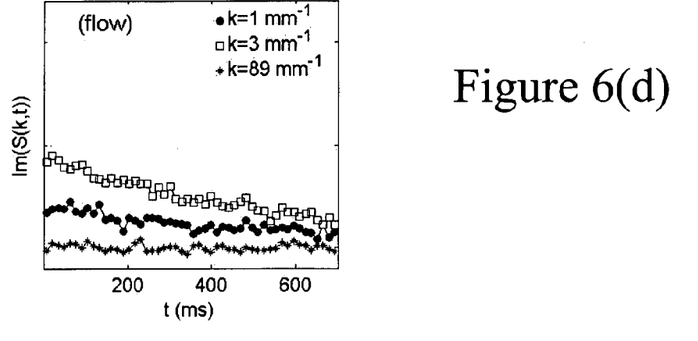
Figure 8A:
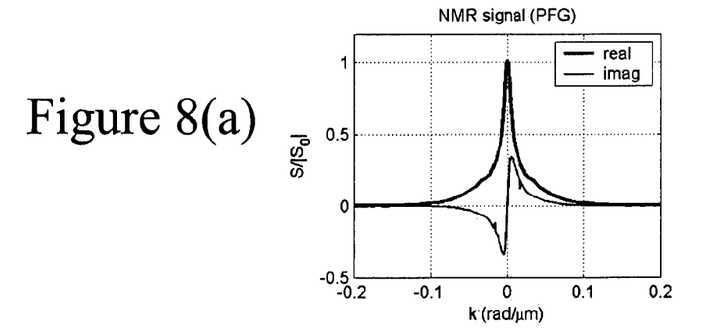
FIGS. 8(a)–(d) are graphs showing NMR flow measurement and analysis obtained of an experiment in a homogeneous magnetic field using the bi-polar PFG-STE sequence of FIG. 5(c), according to standard laboratory practice.
Figure 8B:
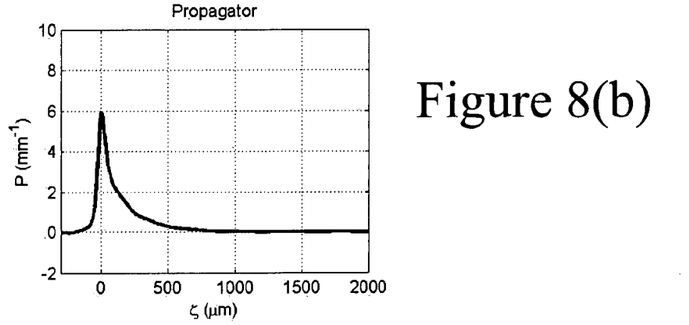
Figure 8C:
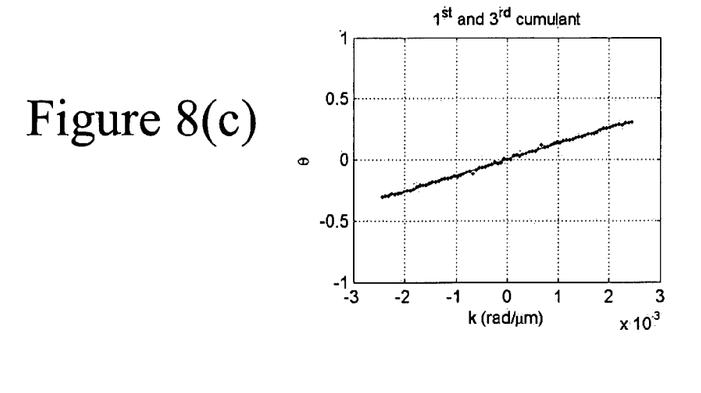
Figure 8D:
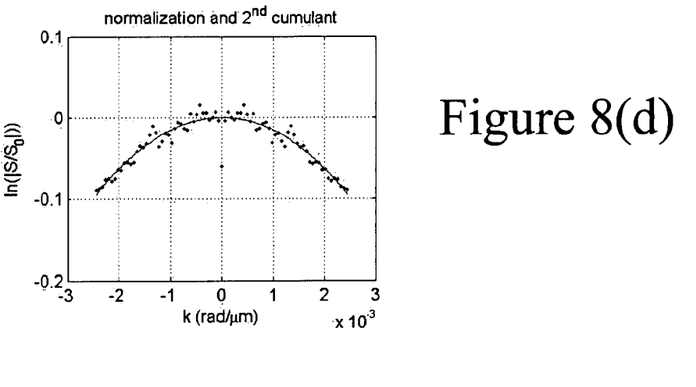
Figure 9A:
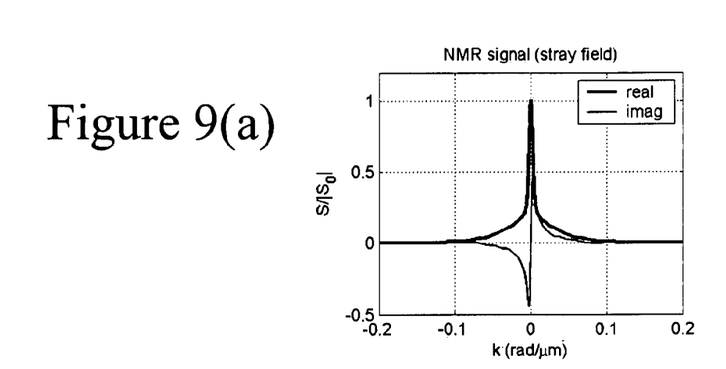
FIGS. 9(a)–(d) are graphs showing the data and analysis for results obtained in the stray field on water flowing through Bentheimer core with the same mean flow and evolution time shown in FIGS. 8(a)–(d), according to the invention.
Figure 9B:
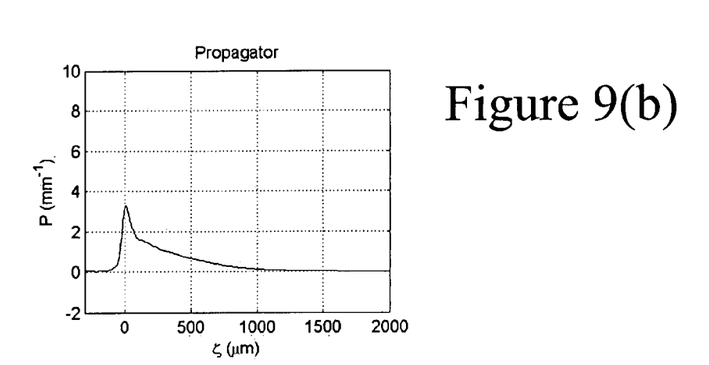
Figure 9C:
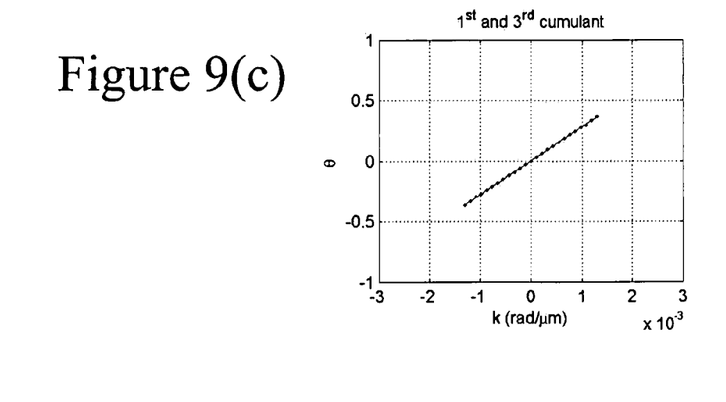
Figure 9D:
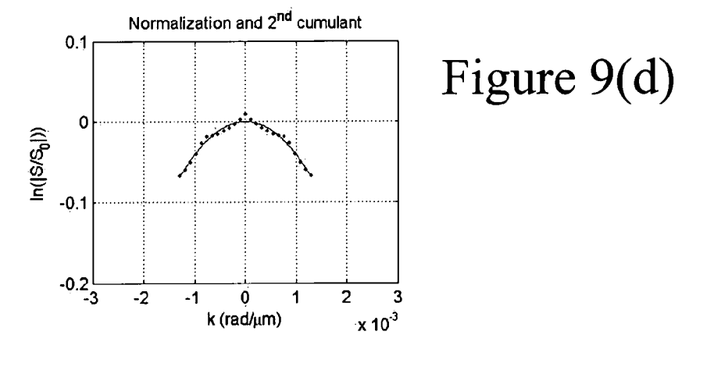

Data and analysis for flow in Bentheimer sandstone obtained with the bi-polar PFG-STE sequence of FIG. 5(c) in the homogeneous 2 Tesla field of a super-conducting NMR magnet is shown in FIGS. 8(a)–(d). This data and analysis was developed using pulsed field gradient experiments known in the art (see Kärger et al., "The propagator representation of molecular transport in microporous crystallites," J. Magn. Reson. Vol. 51, Issue (1), pages 1–7 (1983) and Sodickson et al., "A generalized k-space formalism for treating the spatial aspects of a variety of NMR experiments," Prog. NMR Spectrosc. Vol. 33, pages 77–108 (2002), incorporated by reference herein in their entireties) and is shown here for reference. FIG. 8(a) the real and imaginary channels of the stimulated echo. Fourier transform of the data produces the probability distribution of molecular displacements of un-relaxed spins as shown in FIG. 8(b). For small k fitting, the phase of the data to a linear plus cubic term quantifies the first and third cumulants (i.e., moments) of the displacement distribution, as shown in FIG. 8(c). Fitting the logarithm of the magnitude of the data to a quadratic term measures the second cumulant or moment of the displacement distribution. These quantities are predominantly controlled by the mean flow speed, the evolution time, and the hydraulic connectivity of the pore space. The mean flow velocity was 0.41 mm/s, the evolution time was 320 ms and water was flowing through a Bentheimer core.

FIGS. 9(a)–(d) show the data and analysis for results obtained in the stray field on water flowing through a Bentheimer core with the same mean flow and evolution time as in FIGS. 8(a)–(d), using the method and apparatus of the present invention. The data for negative k are completed by complex conjugation of the data at positive k.

In stray fields, propagators and cumulants can be measured to characterize the pore space. The agreement between PFG and stray field is adequate; the differences are due to experimental artifact, possibly due to the fact that the relationship between the spatial wave vector k and δ ceases to be linear once the encoding interval δ is on the order of the RF pulse duration or the ring down time of the NMR antenna. This effect can be calibrated or modeled and better quantitative agreement between PFG results and stray field results attained, if desired.

While the invention has been described herein with reference to certain examples and embodiments, it will be evident that various modifications and changes may be made to the embodiments described above without departing from the scope and spirit of the invention as set forth in the claims. For example, the apparatus and method may be used for medical applications, food processing applications, flow metering applications, and chemical applications, or pulsed field gradients may be applied to modify the strength and direction of the displacement encoding gradient.

What is claimed is:

1. A method of measuring characteristics of a flowing fluid, comprising:
 a) providing a flowing fluid;
 b) applying a background static field gradient to said flowing fluid;
 c) applying a series of nuclear magnetic resonance pulses to said flowing fluid;
 d) detecting signals from said flowing fluid, wherein said signals are generated in response to said nuclear magnetic resonance pulses; and
 e) analyzing the real and imaginary components of said signals in view of the background static field gradient to determine one or more characteristics of said flowing fluid.

2. The method of claim 1, wherein said flowing fluid is a fluid in a pipe.

3. The method of claim 1, wherein (a) includes inducing said fluid to flow.

4. The method of claim 1, wherein said flowing fluid is a fluid in a porous medium.

5. The method of claim 4, wherein (e) includes determining the flow rate of said fluid in said porous media.

6. The method of claim 4, wherein (e) includes determining the probability distribution for molecular displacements of said fluid in said porous media.

7. The method of claim 4, wherein (a) includes pumping fluid into a flowline within a tool.

8. The method of claim 4, further comprising determining the flow rate of said fluid in said flowline.

9. The method of claim 4, wherein said flowing fluid is formation fluid and said porous media is a region of earth formation.

10. The method of claim 9, wherein (a) includes pumping fluid into a flowline within a tool, wherein said tool is positioned in a borehole traversing said region of earth formation.

11. The method of claim 10, wherein said tool is in contact with the borehole wall and further comprising comparing the flow rate of said fluid in said flowline and the flow rate of said fluid in said region of earth formation to determine the integrity of the contact between said tool and said borehole wall.

12. The method of claim 10, wherein said tool is in contact with the borehole wall and further comprising comparing the flow rate of said fluid in said flowline and the flow rate of said fluid in said region of earth formation to determine the integrity of the borehole wall.

13. The method of claim 10, further comprising analyzing the flow rate of the fluid in said earth formation to identify any localized velocity fields in said region of earth formation.

14. The method of claim 10, further comprising analyzing the flow rate of the fluid in said earth formation to identify the isotropy of permeability of said region of earth formation.

15. The method of claim 10, further comprising comparing the flow rate of said fluid in said flowline and the flow rate of said fluid in said region of earth formation to determine the lithology of said region of earth formation.

16. The method of claim 10, wherein (c) includes pumping fluid into said earth formation thereby displacing said formation fluid.

17. The method of claim 1, wherein said tool is a logging-while-drilling tool and wherein (a) includes allowing drilling mud to passively invade said earth formation thereby displacing said formation fluid.

18. The method of claim 17, further comprising measuring the rate of invasion of the drilling mud.

19. The method of claim 1, wherein said nuclear magnetic resonance pulse sequences are selected from the group consisting of modified Carr-Purcell sequences, modified Carr-Purcell-Meiboom-Gill sequences, or combinations thereof.

20. The method of claim 1, wherein (e) further includes combining detected signals to produce a complex echo train.

21. The method of claim 20, wherein (e) further includes analyzing the real and imaginary parts of the complex echo train to determine the flow rate of the fluid in the earth formation.

22. The method of claim 21, wherein analyzing the real and imaginary parts of the complex echo train includes developing a relationship between spatial magnetization wave vector (k), flow field, and real and imaginary parts of the complex echo train amplitudes.

23. The method of claim 22, wherein the relationship is developed for at least two different values of k.

24. The method of claim 22, wherein the relationship is developed using one value of k and measuring flow field at zero velocity and at one or more finite velocities.

25. The method of claim 1, wherein (a) further comprises using variable encoding times.

26. A nuclear magnetic resonance apparatus to measure characteristics of a flowing fluid, comprising:
- an antenna to create an oscillating magnetic field on a flowing fluid, wherein said antenna is connected to a controller;
- a magnet creating a background static field gradient to said flowing fluid;
- means to detect signals from said flowing fluid generated in response to said oscillating magnetic field; and
- processing means to analyze the real and imaginary components of said signals in view of the background static field gradient to determine one or more characteristics of said flowing fluid.

27. The apparatus of claim 26, wherein said flowing fluid is in a porous media.

28. The apparatus of claim 25, wherein said processing means is programmed to determine the flow rate of said fluid in said porous media.

29. The apparatus of claim 25, wherein said processing means includes means for determining the probability distribution for molecular displacements of said fluid in said porous media.

30. The apparatus of claim 27, further comprising means to pump said flowing fluid into a flowline within a tool equipped with said antenna and magnet.

31. The apparatus of claim 25, wherein said processing means is further programmed to determine the flow rate of said fluid in said flowline.

32. The apparatus of claim 27, wherein said flowing fluid is formation fluid and said porous media is a region of earth formation.

33. The apparatus of claim 32, wherein said tool is positioned in a borehole traversing said earth formation such that said tool is in contact with the wall of said borehole, and wherein said controller is further programmed to compare the flow rate of said fluid in said flowline and the flow rate of said fluid in said earth formation to determine the integrity of the contact between said tool and said borehole wall.

34. The apparatus of claim 25, wherein the processing means is further programmed to compare the flow rate of said fluid in said flowline and the flow rate of said fluid in said earth formation to determine the integrity of the borehole wall.

35. The apparatus of claim 25, wherein the processing means is further programmed to analyze the flow rate of the fluid in said earth formation to identify any localized velocity fields in said earth formation.

36. The apparatus of claim 25, wherein the processing means is further programmed to analyze the flow rate of the fluid in said earth formation to identify the isotropy of permeability of said earth formation.

37. The apparatus of claim 25, wherein the processing means is further programmed to compare the flow rate of said fluid in said flowline and the flow rate of said fluid in said earth formation to determine the lithology of said earth formation.

38. The apparatus of claim 26, wherein said nuclear magnetic pulse sequences is selected from the group consisting of modified Carr-Purcell sequences, modified Carr-Purcell-Meiboom-Gill sequences, or combinations thereof.

39. The apparatus of claim 38, wherein the stimulated echoes or the Hahn echoes of the modified CP or modified CPMG sequences employ variable encoding times.

40. The apparatus of claim 38, wherein said processing means is further programmed to combine sequences to produce a complex echo train.

41. The apparatus of claim 40, wherein said processing means is programmed to analyze the real and imaginary parts of the complex echo train to determine the flow rate of the fluid in the earth formation.

42. The apparatus of claim 41, wherein said processing means is programmed to develop a relationship between spatial magnetization wave vector (k), flow field, and real and imaginary parts of the complex echo train amplitudes.

43. The apparatus of claim 42, wherein the relationship is developed for at least two different values of k.

44. The apparatus of claim 43, wherein the relationship is developed using one value of k and measuring flow field at zero velocity and at one or more finite velocities.

* * * * *